United States Patent [19]
Eyrick et al.

[11] 3,932,066
[45] Jan. 13, 1976

[54] BREATHING GAS DELIVERY CYLINDER FOR RESPIRATORS

[75] Inventors: Theodore B. Eyrick, Reading; Allen C. Brown, Acton, both of Mass.

[73] Assignee: Chemetron Corporation, Chicago, Ill.

[22] Filed: Oct. 2, 1973

[21] Appl. No.: 402,679

[52] U.S. Cl. ............... 417/328; 417/395; 417/473; 128/145.6
[51] Int. Cl.² ............... F04B 17/00; F04B 43/06; F04B 45/02
[58] Field of Search ........ 222/3; 417/328, 395, 472, 417/473, 326; 185/4, 27; 60/397; 128/145.6

[56] References Cited
UNITED STATES PATENTS

| | | | |
|---|---|---|---|
| 983,729 | 2/1911 | Laidley | 417/395 |
| 2,828,694 | 4/1958 | Nallinger | 417/328 |
| 3,242,952 | 3/1966 | Austin | 417/395 X |
| 3,294,030 | 12/1966 | Fox | 417/395 X |
| 3,724,973 | 4/1973 | Shill | 417/326 |

*Primary Examiner*—C. J. Husar
*Assistant Examiner*—Richard E. Gluck
*Attorney, Agent, or Firm*—Jones, Tullar & Cooper

[57] ABSTRACT

A cylinder for delivering at limited positive pressure a preselected limited volume of breathing gas at a preselected limited flow rate. The cylinder includes a cylindrical housing which is substantially closed to the atmosphere. A drive weight is movably mounted within the cylinder, with a rolling diaphragm being connected between the wall of the cylinder and the weight to divide the cylinder into upper and lower chambers. A vacuum source is connected to the upper chamber to draw the weight and diaphragm upwardly, expanding and drawing breathing gas into the lower chamber. By controllably releasing the vacuum in the upper chamber, the weight is allowed to fall downwardly, solely under the force of gravity, to cause the lower chamber to contract. This creates a positive pressure in the lower chamber, forcing the breathing gas out of an outlet for delivery to a patient. The weight is slidably mounted on a hollow tube which extends axially through the housing, and a follower chain connected to the weight passes through the tube to an external indicator. The tube may be slotted to accomodate a connection between the follower and the weight to provide a positive indication of the exact location of the weight, and a bellows arrangement is provided to seal the upper and lower chambers from the area occupied by the tube.

23 Claims, 4 Drawing Figures

BREATHING GAS DELIVERY CYLINDER FOR RESPIRATORS

BACKGROUND OF THE INVENTION

The present invention relates, in general, to respirator apparatus for delivery of breathing gases to a patient, and more particularly to a gas delivery cylinder for providing, at a limited positive pressure, a preselected limited volume of gas at a preselected limited flow rate.

This application is related to copending application Ser. No. 402,677, now U.S. Pat. No 3,905,362, of Theodore B. Eyrick, Allen C. Brown, and Neil R. Hattes, entitled "Volume-Rate Respirator System and Method" filed on even date herewith, and to copending application Ser. No. 402,678, now U.S. Pat. No. 3,887,795, of Theodore B. Eyrick and Neil R. Hattes, entitled "Respiration Ratemeter," filed on even date herewith, the disclosures of which are hereby incorporated herein.

In the treatment of respiratory ailments, in the introduction of anesthetics into the breathing gases of patients, in the control or regulation of a patient's breathing, and in similar and well known uses of respirators or ventilators, it is frequently necessary to provide means for accurately and repeatedly controlling or limiting the volume, flow rate, and pressure of the breathing gases delivered to the patient. Such controls and their accompanying indicators and alarms are necessary in order to avoid not only discomfort, but in many cases outright danger to the patient. Over the years, a great variety of clinical equipment has been developed and employed in the prior art to provide such controls, but the various limitations inherent in the existing devices have created a need for machines of increased reliability, flexibility, capacity, and safety not only to improve the quality of treatment being received by the patient, but to insure his safety against any possible failures of the equipment or its control system.

One of the basic elements in any such respirator system is the unit which receives the breathing gases from a source of supply and which then delivers those gases under pressure through suitable tubing to the patient. Such units have taken a variety of forms in the prior art, with one of the more common units utilizing a mechanical piston to deliver predetermined volumes of air. The piston may be driven, for example, by a variable ratio crank and wheel mechanism connected to an electric motor, but such devices have been found to have certain limitations. For example, such a device is not inherently pressure limiting because of the continuous rotation of the crank and wheel mechanism which serves to mechanically force the piston through a given path on each cycle. Variations in the patient resistance can result in high pressures, and such systems therefore require a pressure relief valve to prevent injury. However, such valves can fail or can with age change in their characteristics, and to this extent are unreliable and unsafe. Additionally, in the devices of this type the maximum rate of flow of the delivered gas is not directly known or controlled and this is a potential source of danger to the patient. Finally, it is very difficult to deliver accurate volumes of gas with such devices because too often the actual rate of delivery is not known.

A common alternative to the piston and cylinder arrangement utilizes a cylinder with an internal bellows which is pneumatically driven by a positive pressure pump. The motion of the bellows is controlled by an external potentiometer which senses the position of the bellows, and by means of a control system which operates solenoid valves to regulate the pneumatic drive lines. Although such systems are satisfactory in many cases, the bellows type device presents some problems since it is difficult to deliver an accurate volume of gas, due to the high compliance of the internal bellows. This compliance allows the position of the bellows to vary from the nominal location, and thus prevents accurate and repeatable delivery of preset volumes of gas. Further, such systems are not inherently pressure limiting, for a failure of the control system during delivery of gas can result in an excessive maximum pressure; accordingly, such systems require a separate pressure relief valve with its attendant shortcomings. The pneumatic drive system normally used with devices of this type presents some difficulty in that such systems are relatively slow to respond to controls, and thus the flow delivery curves are relatively slow. Finally, it is not unusual to find that a substantial portion of the volume of gas to be delivered to the patient remains stored and compressed within the bellows at the end of a delivery cycle, thereby reducing the maximum volume of gas capable of being delivered to the patient.

Other systems of delivering gas to a patient include means for providing a mechanical bias which serves to drive a bellows arrangement. However, such a biasing arrangement presents difficulties in that the flow rate of the system is not limited and it is difficult to deliver accurate volumes of gas due to the high compliance of the bellows and because of variations in characteristics of such devices. Further, in most such devices substantial quantities of gas remain stored within the bellows at the end of a delivery stroke.

SUMMARY OF THE INVENTION

The present invention is directed to an air delivery device for use in respirator systems and which overcomes the difficulties found in prior mechanical and pneumatic devices. A preferred construction is described briefly below to summarize several significant features of this invention.

In its preferred form, the air delivery unit comprises a vertically positioned cylindrical housing containing an axially extending hollow shaft which forms a guide for a movable weight which is mounted by means of suitable bearings on the shaft. A follower chain extends through the hollow central shaft and is attached to the weight and to an external potentiometer, whereby motion of the weight causes a corresponding variation in the output of the potentiometer to provide an indication of the exact position of the weight within cylinder. A rolling diaphragm seals the circumference of the sliding weight to the inner surface of the cylindrical housing to form a weighted piston which divides the housing into an upper and lower chamber. The chambers are sealed from the central shaft by means of upper and lower bellows which are secured between the sliding weight and the upper and lower ends of the housing, and surround the shaft.

A vacuum pump is connected to the upper chamber through a control valve, while the lower chamber is open to a supply of breathing gas through an inlet check valve and to the patient's lungs through an outlet check valve, the valves serving to insure the proper direction of flow. Application of a vacuum to the upper chamber allows the breathing gas, which is at ambient or slightly higher pressure, to force the sliding weight upwardly to a preselected position. The location of the weight is sensed by the potentiometer so that the control valve can be closed when the weight approaches the desired level.

Also connected to the upper chamber is a bleeder valve which is variable to allow the vacuum in the upper chamber to be released at a predetermined rate. By admitting ambient air into this upper chamber, the sliding weight is allowed to move downwardly under the force of gravity to force the breathing gas out of the lower chamber outlet at a preselected rate. Thus, the lower chamber is filled with breathing gases such as air, oxgen, or anesthetic gases while the weight is being lifted, and when the weight is released the selected volume of breathing gas is delivered to the patient at a preselected flow rate that is limited by the setting of the bleeder valve.

An air delivery cylinder so constructed overcomes substantial difficulties encountered with prior art devices, and provides a highly accurate, repeatable delivery of preselected volumes of air at preselected rates, with a high degree of safety. Because of the use of a rolling diaphragm arrangement wherein the control, or upper chamber is separated from the lower, or delivery chamber by a flexible diaphragm which rolls along the wall of the cylinder housing as the weight moves up and down, the delivery chamber has a very low compliance. This permits accurate control of the volume and pressure of the gas being delivered to the patient.

The use of a sliding weight to provide the driving force on the delivery stroke of the cylinder produces a distinct improvement over prior devices in that the air delivery system is inherently safe and does not have to rely on complex control systems to protect the patient. This is due to the fact that the maximum pressure that can be generated in the delivery chamber under any condition is that produced by the force of gravity acting on the weight. This weight is selected, in the design of the cylinder, to have a mass which will produce only a known maximum pressure even under free falling conditions within the cylinder, and the system is therefore self-pressure limiting. Accordingly, the need for pressure relief valves and the like is avoided, and this not only reduces the complexity and cost of the cylinder, but provides a greater margin of safety for the patient with fewer components than are required in prior art systems.

Since the weight remains constant as it moves down the central shaft of the cylinder during a delivery stroke, the flow of gas to the patient is not affected by cylinder compliance, variations in mechanical drive devices, or the like, and accordingly, the cylinder produces exceptionally good flow delivery characteristics. This flow is an inverse function of the breathing gas pressure produced by the weight, the flow gradually decreasing as the pressure builds up and ceasing at maximum pressure, thereby minimizing patient hazard. Maximum pressure is available throughout the length of the delivery stroke, since the maximum driving force of the weight is always available.

With the present device, the selection of a desired volume of the breathing gas which is to be delivered to the patient is simple, highly accurate, repeatable, and provides an improved safety factor for the patient. In many prior systems, the delivery of a gas is initiated from a point of maximum volumetric content of the delivery cylinder, i.e., with the delivery device containing its maximum air volume, and their control systems operate to terminate the delivery stroke when the desired volume, rate of flow, or pressure has been reached. In such systems, a failure of the control system can result in injury to the patient, for if the control does not work, the full volume of air may be delivered. In the present system, however, control of the volume to be delivered is regulated by the position taken by the cylinder at the end of its upward, or loading stroke; the down, or delivery stroke always ends adjacent the bottom of the cylinder so that only the preselected volume can be delivered, even in the event of a control failure. Because the location of the weight is continuously monitored in the present device, the volume to be delivered to the patient can be determined before the delivery stroke begins, so that if any error or failure of the control system has occured, it can be recognized before the stroke begins. Finally, with the drive weight bottoming on each stroke, deadspace within the cylinder is minimized and virtually the entire capacity of the cylinder is available for delivery to a patient.

The foregoing and additional objects, features, and advantages of the invention will be more clearly understood from a consideration of the following detailed description of a preferred embodiment of the invention, taken with the accompanying drawings in which:

FIG. 4 is a diagramatic view of a pneumatic system for operating the cylinder of FIG. 1.

Figure 1:
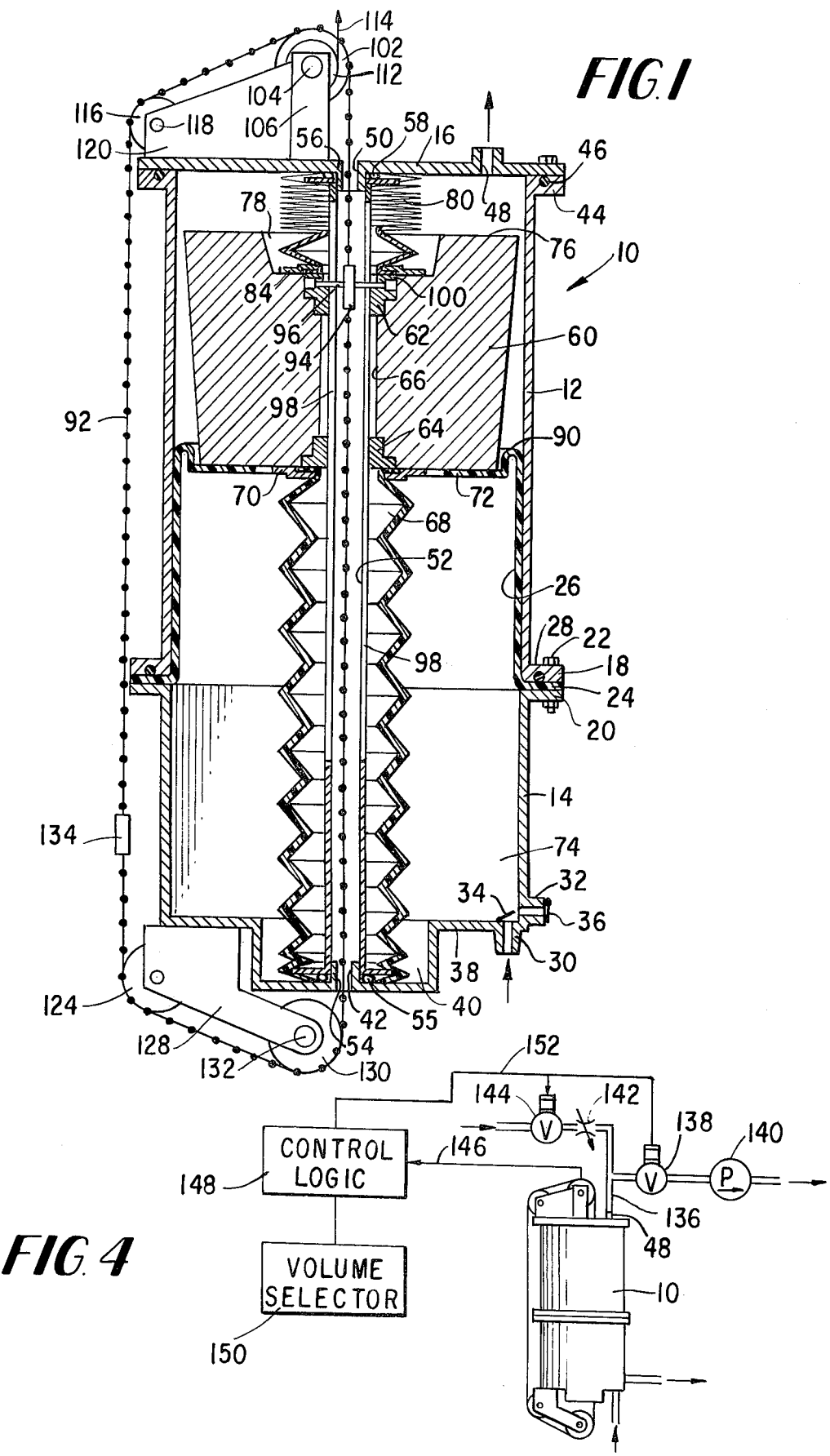
FIG. 1 is a cross-sectional view of a gas delivery cylinder for a respirator made in accordance with the present invention and showing the gas delivery drive weight in an upper or charged position.

Referring now to the drawings, there is illustrated generally at 10 a gas delivery cylinder suitable for use in a respirator system for delivering accurate volumes of gas at limited flow rates and pressures and more particularly for delivering at limited positive pressure a preselected limited volume of gas at a preselected and limited flow rate. The cylinder is formed from an upper cylindrical housing portion 12 which is closed at its lower end by a lower cylindrical housing portion 14 and at its upper end by a cap 16. The housing portion 12 is formed with a peripheral outwardly extending flange 18 which matches a corresponding peripheral flange 20 on the upper edge of the lower cylinder housing portion 14. These flanged portions are adapted to be secured together by means of bolts 22, clamps or other suitable means to form an airtight connection. Clamped between the two flanges is the peripheral edge of an annular rolling diaphragm 24 of conventional construction of the type shown, for example, in U.S. Pat. No 2,849,026. The flexible material of the diaphragm serves as a gasket between the flanges; in addition, to insure an airtight connection, an O-ring 28, separate (as shown) or integral with the diaphragm, may be incorporated in the flange connection.

The lower housing portion 14 is generally cylindrical in shape and includes at its bottom edge an inlet passage 30 and an outlet passage 32, both of which include valve means such as the check valves 34 and 36, respectively, to limit the direction of fluid flow. The inlet 30 and check valve 34 cooperate to permit the flow of gases into the housing portion 14, while outlet passage 32 and check valve 36 cooperate to permit the passage of air from within housing portion 14 to a conduit or the like (not shown) leading to the patient who is to be supplied with breathing gases from the gas delivery cylinder.

The bottom of lower cylindrical housing portion 14 is closed by a bottom portion 38 which preferably is formed as a part of housing portion 14 but which may, if desired, be a separate closure plate. Centrally located in the bottom plate is a concavity, or recess, 40 the purpose of which will be described hereinbelow. Within the recess, and axially located with respect to the cylinder 10, is an aperture 42 which provides acess to the interior of the cylinder.

The upper cylindrical housing portion 12 is provided at its upper edge with the cap 16 which closes the upper end of the cylinder. An O-ring 46 is provided between the flange 44 and the peripheral edge of cap 16 to provide an air tight seal. The cap 16 incorporates a control passageway 48 which permits air to be drawn out of the upper housing portion 12 of the cylinder and which allows air to be returned to that upper portion in order to control the operation of the cylinder. A second aperture 50 is centrally located in cap 16 at the axis of cylinder 10 to provide entry to the interior of the cylinder.

Secured to the interior of cylinder 10 and extending axially therethrough between apertures 42 and 50 is a support tube, or guide shaft 52. The lower end of the cylindrical shaft 52 is adapted to fit around and engage an upstanding flange 54 surrounding the aperture 42 in bottom plate 38, with an O-ring 55 being located between shaft 52 and plate 38 to insure an air tight fit. In similar manner, the upper end of the guide shaft 52 engages a flange 56 which defines the aperture 50 in the cap or top plate 16. An O-ring 58 insures an air tight seal between the guide shaft and flange 56.

Located within the housing defined by the upper and lower portions 12 and 14 of cylinder 10 is a drive weight 60 which is generally annular in shape and is adapted for motion upwardly and downwardly within the cylinder. The weight may be formed from lead to provide the desired mass, and is provided with upper and lower bearings 62 and 64. The bearings are mounted at the upper and lower end of the interior surface 66 of the annular weight and are adapted to slidably engage the exterior surface of guide shaft 52. The bearings preferably are made from a filled Teflon (polytetrafluoroethylene) material to provide long life as well as ease of motion during the up and down cycling of the weight.

Figure 2:
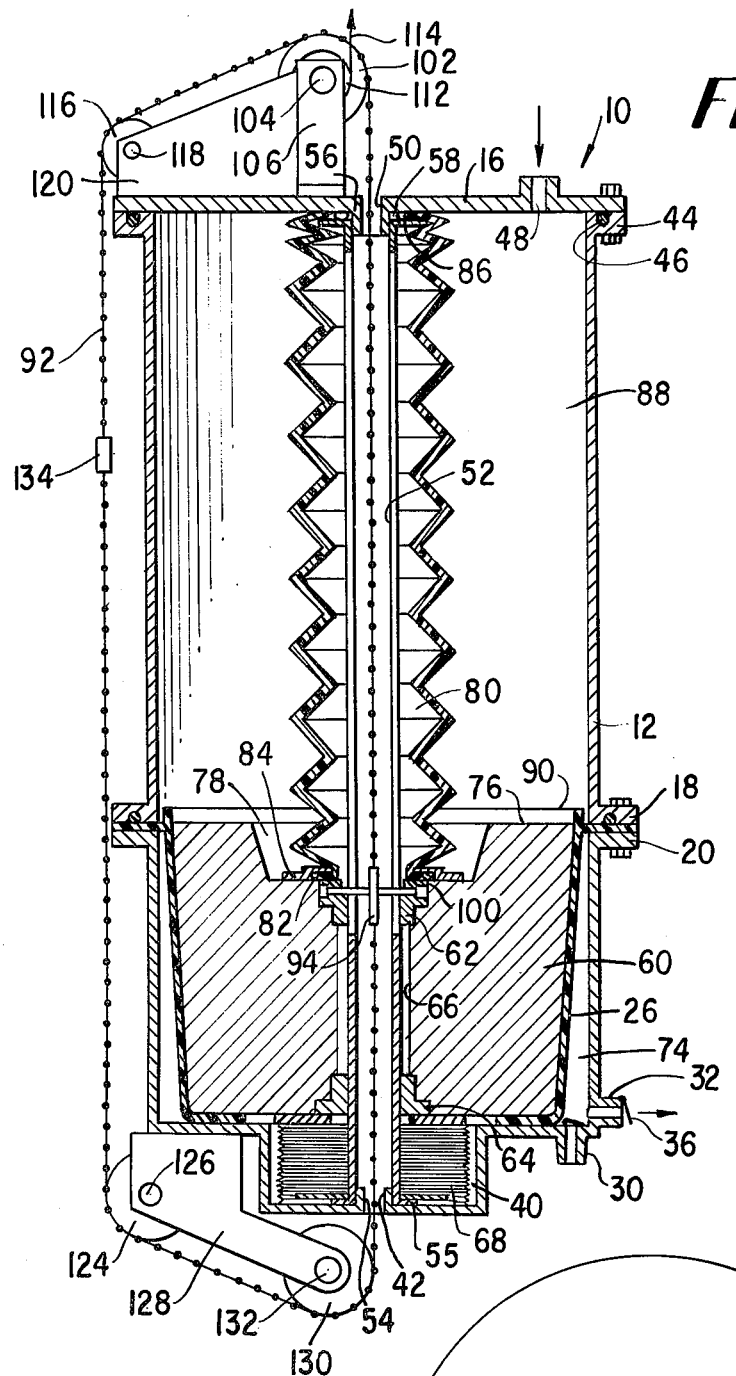
FIG. 2 is a cross-sectional view of the device of FIG. 1, showing the drive weight in its fully lowered or discharged position.

Sealed to the bottom of weight 60, preferably at or adjacent the interior surface 66, is secured the upper peripheral edge of a generally tubular, collapsible bellows 68. The bellows surrounds the lower portion of shaft 52, extending downwardly and being secured to the bottom plate portion of housing 14, as at the O-ring 55. The bottom peripheral edge of the bellows is hermetically sealed to the bottom plate 38 or to the bottom of shaft 52 and is adapted to extend, as in FIG. 1, when the weight 60 slides upwardly on shaft 52 and to collapse into the recess 40 when the drive weight moves downwardly, as illustrated in FIG. 2. The upper peripheral edge of the bellows 68 may be secured and hermetically sealed to the bottom of weight 60 by any suitable means. For example, an annular retaining plate 70 may extend over the upper edge of the bellows and may be secured by suitable means (not shown) to the bottom of the weight to provide an air tight seal, thereby isolating the lower part of the shaft from the interior of the housing. Preferably, the bellows is reinforced, as by rigid polymeric rings (now shown), to withstand internal-to-external pressure differentials without excessive lateral distortion.

Also secured to the bottom surface of weight 60, or to some other convenient portion of the weight, is the inner peripheral edge 72 of the generally annular diaphragm 26. Edge 72 may be secured to the weight by a suitable adhesive, by a retaining ring, or by any other means suitable for providing a hermetic seal between edge 72 and the weight. The annular diaphragm thus extends from the cylindrical wall defined by housing portions 12 and 14 to the movable weight 60; the bottom of weight 60 extends from the inner peripheral edge of the diaphragm 26 to the upper end of bellows 68; and the bellows 68 extends from the bottom of weight 60 to the bottom plate 38 of lower housing portion 14. These elements, together with the housing portion 14, are all air tight and form a lower, or delivery chamber 74 within the gas delivery cylinder 10. This chamber is connected to a source of breathing gas, which may be the atmosphere, by way of inlet 30, and is adapted to be connected to a patient by way of outlet 32.

As may be seen more clearly in FIG. 2, the upper surface 76 of the drive weight 60 is formed with a centrally located recess 78 which is adapted to receive the lower peripheral edge of an upper bellows 80 which is collapsible, generally tubular in shape and adapted to surround the upper portion of shaft 52. Preferably, the bellows 80 also is reinforced as described above. The lower peripheral edge 82 of the bellows 80 may be secured to the weight 60 by any suitable means such as a retainer ring 84 secured in the bottom of recess 78 and providing an air tight seal between the bellows and weight 60.

The upper peripheral edge 86 of the bellows 80 is sealed to the cylinder cap 16 or to the upper end of the guide shaft 52 by any suitable means to form an air tight seal with the container housing so that the rolling diaphragm 26, the drive weight 60, and the bellows 80 cooperate with the cylindrical housing portion 12 and the cylinder cap 16 to form an upper control chamber 88, which chamber is isolated from the guide shaft and is connected to the exterior of the container 10 only by way of the control passage 48.

It will be seen from FIG. 2 that when the drive weight 60 is in its lower position, the bellows 80 is extended to cover shaft 52, while bellows 68 collapses into recess 40 at the bottom of the cylinder. When the weight is raised, as illustrated in FIG. 1, the upper bellows 80 collapses into recess 78 while bellows 68 extends to cover the lower portion of shaft 52. The bellows 68 and 80 are formed of a polyurethane material, preferably reinforced as described above, which is flexible enough to permit easy movement of the weight, but which has a substantial memory so that each time they are extended, as is bellows 68 in FIG. 1, they will return to their proper shapes and the volume of at least the lower chamber 74 will be essentially constant for a predetermined location of the weight. Since in the operation of this system, it is necessary to have a known volume of gas in chamber 74, so that a known quantity of gas can be delivered to the patient; the memory feature of the reinforced material used for bellows 68 is particularly important. The gas drawn into the chamber 74 through inlet 30 during an upward motion of weight 60 and the gas in the chamber just prior to a delivery stroke is normally at or about atmospheric pressure, and since the interior of the bellows is also at atmospheric pressure, as will be seen, no difficulty has been found (in actual tests) in assuring the desired volumetric measurements.

In accordance with the present invention, the cylinder is so designed and operated that each delivery stroke of the weight and rolling diaphragm ends with the weight adjacent the bottom of the housing, as indicated in FIG. 2. The bellows 68 is virtually collapsed when the weight 60 reaches the end of the downstroke, and accordingly any flexing of the bellows that might be caused by increased pressure in chamber 74 due to the downward motion of weight 60 will not significantly affect the volume of air delivered, for by design the chamber 74 will have essentially the same volume at the end of each stroke; such volume precisely depends upon final inertia of the lowering weight, but in all cases is minimal. Further, it will be seen that the flexible diaphragm 26 rolls along the inner wall of the upper housing portion 12 and along the outer surface of the weight 60 during vertical motion of the weight, and is thus always supported by a solid wall portion except at that part of the diaphragm which bridges the space between drive weight 60 and the cylinder housing. However, since this bridging area, indicated at 90 in FIGS. 1 and 2, is relatively small as well as being a curved surface, there is a negligible amount of flexing due to the pressure of air in chamber 74, again as shown in U.S. Pat. No. 2,849,026. Thus, the memory effect of the bellows 68, which provides a constant volume at the start of a downstroke, taken with the low compliance of diaphragm 26 and the fact that bellows 68 is virtually collapsed at the end of the downstroke, or delivery stroke, insures that with minimal deviation, a known quantity of breathing gas will be delivered by cylinder 10 during each cycle. Further, for a given starting location of drive weight 60, this quantity will be essentially constant for each cycle of operation. Thus, the present device is of extremely low compliance, and thereby provides a high degree of accuracy in the delivery of preselected quantitites of breathing gas.

To provide accurate monitoring of the location of the drive weight 60, and thus to provide accurate readings of the volume of chamber 74, a follower chain 92 is secured to the drive weight for motion therewith. As illustrated in the drawings, the chain may be secured to the drive weight 60 by means of a coupler 94 attached at its upper and lower ends to corresponding ends of the chain. The coupler is secured to the drive weight 60 by means of a pin 96 which passes through a longitudally extending slot 98 formed in the guide shaft 52. The opposite ends of pin 96 are then secured at diametrically opposed points within the recess 78 of weight 60, with the pin being secured for motion with weight 60 by means of a retainer washer 100. Washer 100 is annular in shape with its inner periphery being spaced from shaft 52 and its outer periphery engaging the walls of recess 78 to hold pin 96 in place for movement with the weight 60. If desired, the washer 100 may in turn be secured in place by the retainer ring 84, or the washer may be independently secured in the recess. It will be noted that slot 98, which extends diametrically across the guide tube 52, is provided along most of the length of the guide tube so that pin 96 may move freely with weight 60 as the weight slides up and down the tube.

This slot provides communication between the exterior of the housing and the interior of the bellows 68 and 80 by way of the hollow tube 52 and housing apertures 42 and 50, and thereby assures atmospheric pressure inside the housing.

Figure 3:
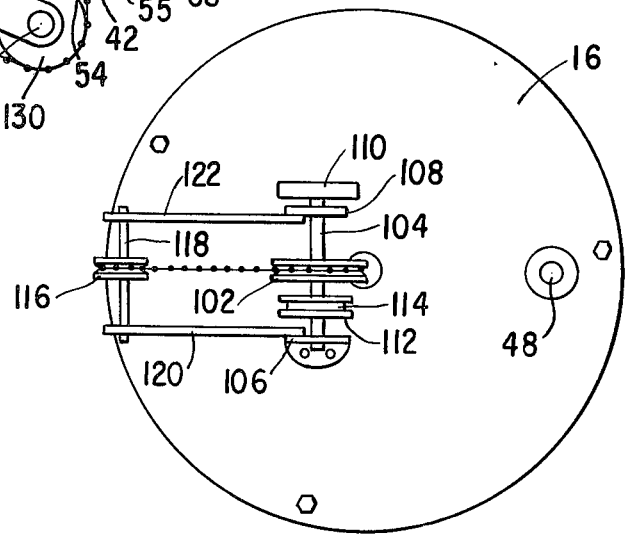
FIG. 3 is a top view of the cylinder of FIG. 1.

The portion of the follower chain which is secured to the upper end of coupler 94 extends upwardly through the hollow center of support tube 52 and passes out of container 10 through the upper aperture 50. The chain passes over a potentiometer drive pulley 102 carried on a support shaft 104 (FIG. 3) journaled at its end in support frame 106 and 108 secured to the top surface of cap 16.

The drive shaft 104 drives a potentiometer 110 to produce a resistance which varies in accordance with the vertical position of weight 60. The output of the potentiometer may be utilized to operate suitable indicator means, control circuits, or the like (not shown). Shaft 104 also drives an indicator pulley 112 connected by way of a cable 114 to a mechanically operated volume indicator (not shown) which moves in accordance with the motion of weight 60 to provide a continuing visual indication of the motion and position of the drive weight.

After passing over drive pulley 102, the follower chain 92 extends radially across the cap 16 to an idler pulley 116, mounted for rotation on a shaft 118 journaled for rotation in a pair of frame members 120 and 122. The chain then extends downwardly along the exterior of container 10 to a second idler pulley 124 carried by a shaft 126 journaled in a frame member 128 secured to the bottom plate 38 of the cylinder. The chain passes around a third idler pulley 130 carried by shaft 132 also mounted in the frame 128; through the lower aperture 42 formed in the bottom plate and passes upwardly through guide shaft 52 to be secured to the lower end of the chain coupler 94. If desired, a tension means such as a spring 134 may be provided in the chain to insure that it remains taut, thereby eliminating lost motion between the weight and the potentiometer and assuring accurate readings.

The operation of the breathing gas supply cylinder 10 may be seen from the diagrammatic illustration of the cylinder and a portion of an associated control system as illustrated in FIG. 4. In this figure, the control aperture 48 of the cylinder is shown as being connected through a conduit 136 and through a solenoid-controlled valve 138 to a vacuum pump 140 which, when valve 138 is open, draws air out of the upper control chamber 88 of cylinder 10. The control aperture is also connected by way of conduit 136 to a variable flow limiting valve 142 and a second solenoid-controlled valve 144 to atmosphere. When solenoid valve 138 is closed and valve 144 is opened, atmospheric air can bleed through the variable flow control orifice 142 into conduit 136 and thence through control passage 48 into the control chamber 88. The system shown in FIG. 4 is a highly abbreviated version of the system preferred for use with the breathing cylinder; for a more complete description of the system and its operation reference is made to copending application Ser. No. 402,677, now U.S. Pat. No. 3,905,362, of Theodore B. Eyrick et al. and application Ser. No. 402,678, now U.S. Pat. No. 3,887,795, of Theodore B. Eyrick et al. referred to hereinabove.

When valve 144 is closed and valve 138 is opened, the pump 140 produces a vacuum in chamber 88 which causes the drive weight 60 to be drawn upwardly along the guide shaft 52. As the weight is lifted, the bellows 80 gradually collapses, the bellows 68 gradually extends, the diaphragm 26 is rolled up along the interior wall of housing portion 12, and chamber 74 expands. The breathing gas from a source such as atmosphere, a supply of oxygen, a supply of anesthetic gas, a combination of such sources, or the like, flows into the inlet 30 and through valve 34 filling in breathing chamber 74.

The upward motion of the drive weight is sensed by the rotation of the potentiometer 110 which produces an electrical signal which may be fed, for example by way of a connecting line 146, to suitable control circuitry generally indicated at 148. This control circuitry may provide means 150 for presetting the desired volume that is to be delivered by the breathing cylinder. The selected volume corresponds closely to a specific location of the drive weight 60 along the support shaft 52 and when this position is attained, the signals from the selector 150 and the potentiometer will correspond, and a control signal will be sent by way of line 152 to the solenoid control for valve 138, shutting off the valve and preventing further withdrawal of air from control chamber 88. The weight will come to a halt, and remain in a raised, or loaded position indefinitely, until it is desired to deliver the selected volume of air.

To initiate the delivery of breathing gas, the control logic circuit 148 will provide a signal to the solenoid control for valve 144, opening the valve to allow air to flow into chamber 88 through orifice 142 to release the drive weight and allow it to slide downwardly under the force of gravity. The setting of orifice 142 controls the rate at which air can bleed into chamber 88, and thus limits the rate at which the drive weight can descend. The downward motion of the drive weight creates a pressure on the gas in chamber 74, forcing the gas out of the outlet 32 and through check valve 36 to a suitable conduit, breathing mask, or the like which directs the discharged breathing gas to the patient.

By presetting the upper location of the drive weight, the desired amount of breathing gas is selected prior to the start of the delivery stroke, so that a failure of the control system during the delivery stroke can not result in a greater amount of gas being delivered. The passageway 48 may be restricted so that even if, for example, the conduit 136 is removed from the control passage 48, during a discharge cycle, the weight cannot descend freely against the back pressure provided by the output passage 32 and the patient's lungs. Furthermore, the mechancial monitoring of the position of weight 60 permits the operator to ascertain the volume that is to be delivered on the next delivery cycle, so that even if the control system fails on the upstroke of weight 60 and does not properly locate the weight for delivery of the selected volume, the operator has an opportunity to correct the error. Thus, by controlling the upstroke in this manner, it is possible to obtain monitoring of the system before delivery, thereby providing an important safety factor.

In the present system, a sufficiently high vacuum is provided to insure a very fast lifting of the drive weight 60 so that the system is charged quickly and is held ready for a subsequent delivery stroke. This not only allows extra time for checking the volume to be delivered, but also provides a quiescent period during which the location of the weight will stabilize prior to the next delivery cycle, allowing an accurate measure of the volume to be delivered. Further, since the control takes place during upward motion of the weight, any overshoot that might occur in the system occurs on the loading cycle, rather than on the discharge cycle, thus providing an additional safety factor.

In a preferred embodiment of the delivery chamber of the present invention, it was found that by providing a stroke of 20.2 centimeters in a cylinder housing 12.7 centimeters in diameter a displacement of 2.1 liters could be obtained in the delivery chamber, giving the system an adequate delivery volume. It has been found that a drive weight of 12.1 kilograms will provide a maximum effective pressure of 100 centimeters of water, taking into account the actual operating conditions of such a cylinder. The effective area (for volume meansurements) of diaphragm 26 is 104 square centimeters. The foregoing data are approximate and take into consideration a lower bellows 68 nominally 5.5 centimeters in outside diameter. Thus, there has been disclosed a new and improved breathing gas delivery cylinder which is capable of delivering at limited positive pressures a preselected volume of gas at a preselected limited flow rate. Although a specific embodiment of a preferred form of the cylinder has been described, it will be apparent to those skilled in the art that numerous variations and modifications can be made without departing from the true spirit and scope of the invention as described in the following claims.

What is claimed is:

1. In a fluid delivery cylinder for delivering at limited positive pressures a selectable, limited volume of fluid at a selectable, limited flowrate:
   housing means;
   diaphragm means dividing said housing into an upper control chamber and a lower delivery chamber;
   guide means extending vertically through and secured to said housing;
   fluid delivery drive means within said housing including a weight slidably mounted on said guide means and secured to said diaphragm means for movement therewith;
   bellows means connected between said fluid delivery drive means and said guide means to isolate said control chamber from said delivery chamber,
   means for producing a vacuum in said control chamber for lifting said drive means to contract said control chamber and expand said delivery chamber to a preselectable volume;
   inlet means for admitting fluid into said delivery chamber when said drive means is lifted;
   means for releasing said vacuum to lower said drive means and thereby compress said delivery chamber; and
   outlet means for discharging fluid from said delivery chamber when said drive means is lowered.

2. The apparatus of claim 1, wherein said weight has sufficient mass to drive said fluid out of said delivery chamber against positive fluid outlet pressure, said fluid being driven at a pressure and rate limited by the mass of said weight and controlled by said means for releasing said vacuum.

3. The apparatus of claim 1, wherein said diaphragm means comprises a rolling diaphragm secured between the inner wall surface of said housing and said drive means, said drive means being closely spaced from said wall surface so that the lifting and lowering motion of said drive means causes said diaphragm to roll along the inner wall surface of said housing and the outer surface of said drive means, whereby said delivery chamber has low compliance.

4. The apparatus of claim 1, wherein said guide means comprises a support tube axially secured within said housing, and wherein said drive means comprises an annular weight slidably mounted on said support tube, said weight having sufficient mass to drive said fluid out of said delivery chamber against positive fluid outlet pressures.

5. The apparatus of claim 4, further including means for providing an indication of the motion of said annular weight.

6. The apparatus of claim 5, wherein said support tube is hollow, with the interior of said support tube opening to the exterior of said housing, said means for indicating the motion of said annular weight including follower means movable within the interior of said support tube.

7. The apparatus of claim 6, further including a slot in the wall of said support tube, and linking means extending from said follower means and through said slot to mechanically link said follower means to said weight.

8. The apparatus of claim 7, wherein said bellows means comprises a first bellows connected between said weight and said support tube to isolate said control chamber from said slot in said support tube and from the interior of said support tube, and a second bellows connected between said weight and said support tube to isolate said delivery chamber from said slot in said support tube and from the interior of said tube.

9. A gas delivery cylinder for delivering at limited positive pressures a limited volume of gas at a limited flowrate, comprising:
a substantially closed housing;
guide means secured within said housing to define a generally vertical path;
gas delivery drive means movably mounted within said housing for motion along the path defined by said guide means;
diaphragm means secured between the interior surface of said housing and said drive means for dividing the interior of said housing into an upper control chamber and a lower delivery chamber;
a control passage leading from the exterior of said housing to said control chamber;
inlet means for admitting gas into said delivery chamber;
outlet means for discharging gas from said delivery chamber, said inlet means and outlet means cooperating with said drive means and said diaphragm means to draw gas into said delivery chamber upon upward motion of said drive means and to discharge gas under pressure upon downward motion of said drive means; and
bellows means cooperating with said drive means and said guide means for isolating said control and delivery chambers from each other and from said guide means.

10. The apparatus of claim 9, wherein said drive means comprises a weight having sufficient mass to discharge gas through said outlet against positive gas outlet pressures, the mass of said weight producing the required discharge pressure for said gas.

11. The apparatus of claim 10, wherein the mass of said weight is selected to produce a predetermined maximum pressure on the gas in said delivery chamber, and said control passage is sized to produce a predetermined maximum rate of flow of gas through said outlet.

12. The apparatus of claim 11, wherein said weight is generally annular in shape and surrounds and is slidably mounted on said guide means for vertical motion thereon.

13. The apparatus of claim 11, further comprising means including said control passage for producing a vacuum within said control chamber for contracting said control chamber to lift said weight and thereby expand said delivery chamber and for releasing said vacuum at a selected rate to allow said control chamber to expand, whereby said weight will fall downwardly to thereby compress and discharge the gas in said delivery chamber.

14. In a respirator, a breathing gas delivery cylinder for delivering a limited positive pressures a selectable volume of breathing gas at a limited flowrate,
a substantially closed housing;
fixed guide means secured within said housing;
gas delivery drive means mounted within said housing for motion along said guide means and dividing said housing into an upper control chamber and a lower delivery chamber;
a control passage leading from the exterior of said housing to said control chamber;
inlet means for admitting breathing gas into said delivery chamber;
means connected to said control passage for producing a vacuum in said control chamber for lifting said drive means a predetermined distance, the lifting of said drive means expanding said delivery chamber and drawing in a predetermined volume of breathing gas;
outlet means for discharging breathing gas under pressure from said delivery chamber;
means connected to said control passage for releasing at a selected maximum rate the vacuum in said control chamber to allow said drive means to be lowered by gravity to compress said delivery chamber and pressurize the breathing gas therein, the gas so pressurized being discharged through said outlet means; and
bellows means secured between said drive means and said guide means for isolating said control and discharge chambers from each other and from at least a portion of said guide means, whereby the only access to said control chamber is by way of said control passage and the only access to said delivery chamber is by way of said inlet and discharge passages.

15. The apparatus of claim 14, wherein said drive means comprises a weight slidably mounted within said housing.

16. The apparatus of claim 15, wherein said drive means further comprises a rolling diaphragm secured between the interior surface of said housing and said weight.

17. The apparatus of claim 15, wherein said guide means includes a support tube extending axially within said housing, said weight being annular and mounted for axial motion along said support tube.

18. The apparatus of claim 14, wherein said drive means includes a weight and low compliance rolling diaphragm means connected between said weight and said housing, the motion of said weight causing said diaphragm to roll along the inner surface of said housing and the outer surface of said weight to provide accurate control of the volume of breathing gas drawn into and discharged by said discharge chamber.

19. The apparatus of claim 14, wherein said guide means comprises a support tube secured at each end to said housing and supporting said drive means for substantially vertical movement between said control and delivery chambers, said drive means comprising a weight and diaphragm means connected between said weight and said housing whereby the mass of said weight determines the maximum pressure of said breathing gas and the rate of downward motion of said weight limits the flowrate of said breathing gas.

20. The apparatus of claim 17, wherein said bellows means for isolating said control and discharge chambers comprises a first collapsible bellows connected between the top of said weight and said support tube and a second collapsible bellows connected between the bottom of said weight and said support tube.

21. The apparatus of claim 14, wherein said guide means extends axially through said housing, and wherein said bellows means is generally tubular in shape and is secured coaxially with and surrounding said guide means between said drive means and said housing.

22. The apparatus of claim 21, wherein said bellows means is reinforced by spaced, rigid rings to enable said bellows means to withstand pressure differentials without excessive distortion, whereby the volume of at least said discharge chamber will have predetermined values at predetermined locations of said movable drive means.

23. The apparatus of claim 22, wherein said drive means further includes a low compliance rolling diaphragm secured between said weight and the interior surface of said housing, said weight being spaced from the said interior surface of said housing so that the motion of said weight along said guide means will cause said diaphragm to roll along said inner surface of said housing and along the outer surface of said weight to provide accurate control of the volume of breathing gas drawn into and discharged by said discharge chamber.

* * * * *